(12) United States Patent
Peters et al.

(10) Patent No.: US 9,307,923 B2
(45) Date of Patent: Apr. 12, 2016

(54) ELECTROPHYSIOLOGICAL MONITORING OF UTERINE CONTRACTIONS

(71) Applicant: NEMO HEALTHCARE B.V., Eindhoven (NL)

(72) Inventors: Christiaan Hendrik Leonard Peters, Rosmalen (NL); Rik Vullings, Venray (NL)

(73) Assignee: NEMO HEALTHCARE B.V., Eindhoven (NL)

( * ) Notice: Subject to any disclaimer, the term of this patent is extended or adjusted under 35 U.S.C. 154(b) by 216 days.

(21) Appl. No.: 13/726,293

(22) Filed: Dec. 24, 2012

(65) Prior Publication Data

US 2014/0180169 A1   Jun. 26, 2014

(51) Int. Cl.
*A61B 5/00* (2006.01)
*A61B 5/0488* (2006.01)

(52) U.S. Cl.
CPC ........... *A61B 5/04882* (2013.01); *A61B 5/4356* (2013.01); *A61B 5/725* (2013.01)

(58) Field of Classification Search
CPC .............. A61B 5/7203; A61B 5/4356; A61B 5/04882; A61B 5/725; A61B 5/72–5/7296
USPC .......................... 600/588, 546, 591
See application file for complete search history.

(56) References Cited

U.S. PATENT DOCUMENTS 4,256,118 A * 3/1981 Nagel ........................ 600/546
6,421,558 B1 * 7/2002 Huey et al. ................ 600/546
6,816,744 B2 * 11/2004 Garfield et al. ............ 600/546
7,333,850 B2 * 2/2008 Marossero et al. ........ 600/511
2012/0150010 A1    6/2012 Hayes-Gill et al.

FOREIGN PATENT DOCUMENTS

WO      WO 02/096288       12/2002

OTHER PUBLICATIONS

European Search Report of dated Feb. 27, 2013.
Rabotti et al, "Relationship between electrohysterogram and internal uterine pressure: a preliminary study," Proceedings of the 28th IEEE, EMBS Annual International Conference, NY, USA, Aug. 3-Sep. 3, 2006, pp. 1661-1664.

(Continued)

*Primary Examiner* — Devin Henson
*Assistant Examiner* — David J McCrosky
(74) *Attorney, Agent, or Firm* — Nixon & Vanderhye PC

(57) ABSTRACT

A signal processing arrangement 130, a monitoring system 100, a signal processing method, a monitoring method of monitoring uterine contractions of a pregnant woman, and a computer program product are provided. The signal processing arrangement 130 receives an electrophysiological signal 116 representing uterine muscle activity of a pregnant woman at an input 132. A filter 136 generates a filtered electrohysterogram signal from the electrophysiological signal 116. The filter 136 allows the passage of spectral components between 0 and 3 Hz. A window function applicator 138 applies a window function to the filtered electrohysterogram signal to obtain an output waveform 146. The window function defines that samples of a time interval preceding the application of the window function need to be used The output waveform 146 simulates output data of tocodynamometer or an intra-uterine pressure catheter. The output waveform 146 is provided at an output 144 of the signal processing arrangement.

18 Claims, 6 Drawing Sheets

(56) References Cited

OTHER PUBLICATIONS

Rabotti et al, "Estimation of internal uterine pressure by joint amplitude and frequency analysis of electrohysterographic signals," Physiol. Meas. 29, Institute of Physics and Engineering in Medicine, UK, 2008, pp. 829-841.

Devedeux et al., "Uterine electromyography: A critical review", *Current Development*, 1993, pp. 1636-1653.

* cited by examiner

ELECTROPHYSIOLOGICAL MONITORING OF UTERINE CONTRACTIONS

FIELD OF THE INVENTION

The invention relates to a device for and a method of monitoring uterine contractions.

BACKGROUND OF THE INVENTION

For more than three decades, the worldwide standard for monitoring fetal condition has been cardiotocography (CTG). Cardiotocography is the simultaneous registration of fetal heart rate and uterine activity. In case of uterine contractions, the umbilical cord may get (partially) occluded. In addition, pressure might be exerted on the fetal head. A healthy fetus generally will respond to these new circumstances by a sudden reduction in fetal heart rate. Whether the fetal heart rate is indeed reduced and also the latency between the actual contraction and the deceleration of fetal heart rate, are important clinical parameters to diagnose fetal wellbeing. Two methods are well-known for monitoring the uterine contractions. The first of these methods consists of an elastic belt that contains a strain gauge to assess the degree of "hardness" of the abdomen. The second method consists of a pressure catheter that is, via the vagina and cervix, inserted into the uterus. The elastic belt with strain gauge is referred to as the tocodynamometer. In case of uterine contractions, the "hardness" of the abdomen increases, which is reflected by the tocodynamometer. With this external method however, it is not always possible to discriminate between uterine contractions and (in)voluntary contractions of the abdominal muscles (e.g. due to movement, coughing, etc.). In addition, in case the tocodynamometer does detect true uterine contractions, both the onset and amplitude of the reflected activity may be unreliable and inaccurate. The invasive catheter, or intrauterine pressure catheter (IUPC), detects the factual pressure inside the uterus, yielding a reliable and accurate representation of uterine activity. However, due to the risks involved, e.g. the catheter has been reported to pierce the placenta, and the fact that the IUPC can only be applied after rupture of the membranes and sufficient dilatation of the cervix, the use of this method in current clinical practice is limited.

Now, from literature it is known that the electrical activity of muscles, recorded as the electromyogram (EMG), can provide an accurate reflection of their mechanical activity. For instance, the contraction and relaxation of the cardiac muscles (myocardium), recorded as a specific variant of the EMG and which is referred to as the electrocardiogram (ECG), is widely used to evaluate the performance of the cardiac muscles. Similarly, the electrohysterogram (EHG; the electrical activity of the uterine muscles or myometrium) is reported to provide information of the performance of the uterine muscles. As a matter of fact, the information in the EHG can be processed and presented in such a way that it mimics the information that can be obtained with the IUPC with the main difference that the EHG can be obtained from standard-issue skin electrodes positioned over the uterus on top of the maternal abdomen. Electrohysterography therefore offers a valuable alternative to the IUPC, as it provides reliable information on uterine activity and is free of risks to mother and fetus and can be applied long before rupture of the membranes.

Several methods and systems have been disclosed that use electrohysterography to provide information on uterine contractions. Most systems are intended to provide a measure for uterine activity, often together with a measure for fetal heart activity, to be used for monitoring fetal condition. The methods that are used to provide this measure for uterine activity are either based on filtering of the electrohysterogram or on spectral analysis of the electrohysterogram. Also, systems have been disclosed that are intended to discriminate between harmless contractions of the uterus and actual contractions that lead to birth. In these systems, either the propagation velocity of the electrical signals across the uterus, or spectral parameters of the electrohysterogram are analyzed.

Published patent application US2012/0150010 discloses an apparatus and a method for detecting uterine activity. The apparatus uses cutaneous electrodes on the maternal abdomen to obtain electrophysiological signals that can be used to obtain fetal and maternal heart rate. The apparatus includes a first input for receiving electrical signals from the cutaneous electrodes and a second input for receiving movement signals indicative of a movement of the maternal body from a movement detector. A signal processor separates a uterine electromyogram signal from fetal and maternal heart rate signals and filters out motion artefacts from the electromyogram using the movement signals. An output presents electrohysterogram (EHG) data from the uterine electromyogram signal.

For monitoring fetal condition, the actual timing between uterine activity and changes in fetal heart rate is of high importance, especially for the diagnosis of late decelerations. Gynaecologists and obstetricians are trained to visually evaluate cardiotocographic recordings that use mechanical measures of uterine activity, either an IUPC or a tocodynamometer. When using electrohysterography for monitoring uterine contractions, it is essential that there is no significant delay in the electrical measure of uterine activity with respect to the mechanical measures, especially at the end of a contraction, as the risk of misinterpretation would exist. However, in all methods that have been proposed, such a delay exists either due to processing that requires a certain amount of data, or due to filter characteristics (such as in the above cited patent application). For example, in the method of the cited patent application, a 0.0166 Hz low-pass filter is used which introduces a relatively large delay in the order of 15 to 20 seconds. As a result, these methods fail to provide an instantaneous output that can directly be used for cardiotocography. Additionally, the electrical measure for uterine activity that is provided by some of the methods suffers from a lack of robustness. Some methods, for example, need to be calibrated for each individual patient or require a learning period for the algorithm that has been used.

SUMMARY OF THE INVENTION

It is an object of the invention to provide a signal processing arrangement for and a signal processing method of processing electrophysiological signals related to uterine contractions which have a relatively short delay between the moment in time when electrophysiological signals related to uterine activity are measured and the moment in time when the processed uterine activity data becomes available to a user or to other devices which uses the processed uterine activity data as input data.

A first aspect of the invention provides a signal processing arrangement. A second aspect of the invention provides a monitoring system. A third aspect of the invention provides a signal processing method of processing electrophysiological signals related to uterine contractions of a pregnant woman. A fourth aspect of the invention provides a monitoring method of monitoring uterine contractions of a pregnant woman. A fifth aspect of the invention provides a computer program product. Advantageous embodiments are defined in the dependent claims.

A signal processing arrangement for processing electrophysiological signals related to uterine contractions of a pregnant woman, in accordance with the first aspect of the invention, comprises an input, a filter, a window function applicator and an output. The input receives an electrophysiological signal that is measured on the abdomen of a pregnant woman. The filter receives the electrophysiological signal and provides a filtered electrohysterogram signal. The filter allows a passage of frequencies of the electrophysiological signal in a first frequency range and attenuates frequencies of the electrophysiological signal outside the first frequency range. The first frequency range is from 0 Hz to 3 Hz. The window function applicator receives the filtered electrohysterogram signal and provides an output waveform. The window function applicator generates the output waveform by continuously applying a window function to samples of the filtered electrohysterogram signal, wherein a single application of the window function comprises adding, according to the window function, samples of the filtered electrohysterogram signal of an interval of time preceding the application of the window function. The output provides the output waveform. The output waveform simulates output data of a tocodynamometer or an intra-uterine pressure catheter, the output data representing data relating to uterine contractions. In the above signal processing arrangement output is generated which is similar to data which may be measured by known devices to measure uterine contractions, such as a tocodynamometer or an intra-uterine pressure catheter. The data of these known devices is the golden standard for representing data which relates to uterine contractions. Thus, the above signal processing arrangement may be used in combination with known devices that require input from such known devices for measuring uterine contractions. Further, the output data of the signal processing may be used to present, e.g. on a display, the output waveform which can be interpreted by a physician who is able to interpret data of a tocodynamometer or an intra-uterine pressure catheter.

The above signal processing arrangement does not introduce unnecessary and unwanted delays in the processing of the electrophysiological signal. When the signal processing arrangement processes the signals in a digital way, the filter and window function may only introduce a limited delay on the onset of a contraction. The window function applicator uses only samples of the past of the filtered electrohysterogram signal and, consequently, does not have to wait for future samples before it is capable of calculating a sample of the output waveform. Thus, the provided output waveform is generated real-time and the window function applicator is such that a delay at the end of a contraction is prevented. Hence, the signal processing arrangement provides, at least with respect to the character of delay, a huge improvement compared to known signal processing solutions which try to simulate simulating output data of a tocodynamometer or an intra-uterine pressure catheter. Therefore, the output waveform may be used by physicians in real-time, which means that the output waveform can be used, for example, in known tocographic applications and specific drawbacks of a tocodynamometer or an intra-uterine pressure catheter are overcome.

The electrophysiological signal comprises signal components which relate to electrical activities in biological cells and tissues. The electrophysiological signal may further comprise noise. At least information of an electrohysterogram is present in the electrophysiological signal when the electrophysiological signal is obtained from measurements at the abdomen of a pregnant woman. The filter is designed to allow the passages of signals of certain frequencies of which it is known that they relate to uterus muscle activity, assuming that the received electrophysiological signal is measured at the abdomen of a pregnant woman. Thus a signal is obtained which mainly comprises information of an electrohysterogram. In the ideal situation all signals with a frequency outside the first frequency range are fully suppressed, however, in practical embodiment, signal of frequencies outside the first frequency range are attenuated to a large extent, for example, at least 20 dB. In another practical embodiment, the response diagram of the filter shows just outside the first frequency range a fast decreasing amplitude response.

The window function applicator calculates for each sample of the output waveform a value that is based on samples of the interval of time which precedes the moment at which the actual new sample of the output waveform is calculated. The window function defines how much the contribution of each sample is to the newly calculated value. The output of the window function applicator is preferably normalized with respect a maximum possible value. For each subsequently calculated sample of the output waveform, the interval of time shifts one sample in time.

The invention is not limited to analogue or digital input and/or input signal. When digital signals are used, the sampling frequency is at least large enough to allow the transfer of relevant information in the respective signals. If, for example, the electrophysiological signal received at the input is an analogue signal, and when the filter is a digital filter, the input of the signal processing arrangement converts the analogue signal to a digital signal with an appropriate sampling frequency. If, for example, the output waveform must be provided as an analogue signal, the output may comprise means for converting the digital signal to an analogue signal. The filter may be implemented as an analogue filter, however, the window function applicator uses samples of the filtered electrohysterogram signal and is, therefore, most probably implemented as a digital processing unit.

In an embodiment, the window function applicator rectifies the filtered electrohysterogram signal before the window function is applied to samples of a rectified filtered electrohysterogram signal. In other words, the window function is applied to absolute values of the filtered electrohysterogram signal.

Optionally, the filter has in the first frequency range an amplitude response which linearly increases, within the limits of a predefined error value, with the frequency. Thus, when within the first frequency range a linearly increasing line is drawn, the amplitude response of the filter may deviate from the linearly increasing line, but the difference between the linearly increasing response and the actual amplitude response must be within the limits of the predefined error value. Optionally, the predefined error value is 6 dB. Optionally, the predefined error value is 3 dB.

The amplitude response of the filter enhances specific components of the electrophysiological signal that relate to uterine contractions. Therefore, by using this specific shaped filter, the output waveform better simulates output data of a tocodynamometer or an intra-uterine pressure catheter.

Optionally, the length of the interval of time is larger than 15 seconds. In an optional embodiment, the length of the interval of time is in the range from 19 to 26 seconds. The width of the window function is carefully chosen such that, at the end of the uterine contraction, delays are prevented. Thus, at the end of the uterine contraction, the end is also in real-time visible in the output waveform. It has been found by the inventors that, when a window function is applied which adds samples according to weight values provided by the window function of at least the last 15, the output waveform advantageously simulates output data of a tocodynamometer or an intra-uterine pressure catheter. When the interval of time has a length in the range from 19 to 26 seconds, the output waveform better simulates output data of a tocodynamometer or an intra-uterine pressure catheter.

Optionally, the window function has a value of one for samples of the filtered electrohysterogram signal which fall within a sub-interval of time from 0 to 15 seconds preceding the moment in time at which the window function is applied. The inventors have found that, in order to simulate the output data of a tocodynamometer or an intra-uterine pressure catheter, it is advantageously to fully use the samples of the 0-15 seconds interval of time preceding the application of the window function. Optionally, the value of the window function is one for the complete interval of time. Optionally, the value of the window function may decrease for samples of the filtered electrohysterogram signal which fall within another sub-interval of time which is in between 15 second to 25 seconds prior to the application of the window function. The window function has a relatively high value at 15 seconds and a relatively low value at 25 seconds.

Optionally, the filter is a band-pass filter and the first frequency range of the filter is a range from 0.1 to 3 Hz.

Optionally, the filter is a band-pass filter and the first frequency range of the filter is a range from 0.3 to 0.8 Hz. If the band-pass filter only allows that frequencies in this more narrow first frequency range are let through, the most relevant information of the electrophysiological signal with respect to uterus contractions are provided to the window function applicator. Thus, the more narrow first frequency range allows a better simulation of output data of a tocodynamometer or an intra-uterine pressure catheter.

Optionally, the input of the signal processing arrangement is configured to receive a plurality of electrophysiological signals each representing uterine muscle activity of a pregnant woman. The signal processing arrangement is configured to combine the plurality of electrophysiological signal into a single electrophysiological signals and the filter receives the single electrophysiological signal. Thus, the signal processing means comprises a signal combiner which combines the plurality of electrophysiological signals into the single electrophysiological signal. Each one of the plurality of electrophysiological signals relates, for example, to a signal provided by a pair of cutaneous electrodes or a pair of capacitive sensors which are brought in contact with the abdomen of a pregnant woman. Thus, more measurements are obtained and the complete information is used by the signal processing arrangement. As such, the signal processing arrangement is capable of providing an output waveform which better simulates output data of a tocodynamometer or an intra-uterine pressure catheter. Optionally, the single electrophysiological signal may be a linear combination of the plurality of electrophysiological signals.

Optionally, the signal processing arrangement further comprises a signal scaling means for scaling the output waveform to a waveform within a predefined dynamic range before the output waveform is provided to the output. The output data of a tocodynamometer or an intra-uterine pressure catheter is, in general, within a specific dynamic range and devices that use the output data of these measurement tools expect the signal to be within such a dynamic range. Therefore, in order to be compatible with the output of these known measurement tools, it is advantageous to scale the output waveform such that the output waveform is at least within this dynamic range. Optionally, the signal scaling means scales the output waveform with a scaling factor that is determined such that a maximum of the output waveform of an interval of time is scaled to 70% of the maximum value of the dynamic range. For example, during 5 minutes of the operation of the signal processing arrangement, a maximum value of the output waveform is determined and after the 5 minutes the scaling factor is adapted to such a value that the maximum value of these 5 minutes scales to about 70% of the maximum value of the dynamic range. This way, when the uterine muscle activity increases in strength, the output waveform may increase but is still within the dynamic range. Optionally, the signal processing means may comprise a user calibration command input means and when a user provides a calibration command, the signal scaling means calculates a new scaling factor which is based on the information of the output waveform of, for example, the last five minutes before receiving the calibration command.

Optionally, the signal processing arrangement comprises an artifact correction means for filtering out, before the output waveform is provided to the output, information from the output waveform which does not relate to uterine contractions. By coincidence, the filter and the window function applicator may generate an output waveform which still comprises information that does not relate to uterine contractions and which reduces the quality of the simulation of output data of a tocodynamometer or an intra-uterine pressure catheter. Such non-relating information is termed an artifact. The artifact correction means is capable of filtering out these artifacts from the output waveform. The artifact correction means may operate in different ways. In one embodiment, the artifact correction means also receives the electrophysiological signal and analyses the electrophysiological signal at frequencies outside the first frequency range to discover whether, for example, the overall electrophysiological signal is distorted at specific moment in time such that, at these specific moments of time possible artifacts in the output waveform may be filtered out of the output waveform. In another embodiment, the artifact correction means also receives the electrophysiological signal and analyses the electrophysiological signal to determine whether, at specific moment in time, noise in the electrophysiological signal may result in artifact creation by the filter and the window function applicator. If such an analysis reveals such artifacts, the artifact correction means may filter out these artifacts. In another embodiment, the artifact correction means receives a plurality of electrophysiological signals and analyses these electrophysiological signals to determine whether, at specific moment in time, noise in the electrophysiological signals may result in artifact creation by the filter and the window function applicator. If such an analysis reveals such artifacts, the artifact correction means may filter out these artifacts, for instance by changing the combination of electrophysiological signals that is provided to the band-pass filter. In a further embodiment, the artifact correction means may receive information of other sensors which are brought in contact with the pregnant woman, such as, for example, an accelerometer which measures whether the abdomen of the woman moves in an x, y or z direction. Such movements may result in the activation of the uterine muscles or in electrical activity in the first frequency range without originating from activation of the uterine muscles or in other distortions of the electrophysiological signals and, as such, they may result in the generation of an artifact.

According to a second object of the invention, a monitoring system for monitoring uterine contractions of a pregnant woman is provided. The monitoring system comprises a physiological measurement system and signal processing arrangement. The physiological measurement system provides the electrophysiological signal and comprises at least two cutaneous or capacitive electrodes for measuring signals of uterine muscle activity of a pregnant woman. The signal processing arrangement is an embodiment of the signal processing arrangements of the first aspect of the invention and the input of the signal processing arrangement is coupled to the physiological measurement system for receiving the electrophysiological signal.

The cutaneous or capacitive electrodes have to be applied to the abdomen of a pregnant woman—in an optional embodiment between the navel and the pubis. A distance between the two cutaneous or capacitive electrodes must be large enough to allow a reliable measurement of signals of uterine muscle activity. The distance between the two cutaneous or capacitive electrodes is, for example, at least 5 centimeters, or, for example, at least 10 centimeters. The physiological measurement system may also comprise other cutaneous or capacitive electrodes, such as an electrode to which a ground voltage is applied. The ground voltage electrode may also be applied to the abdomen of the pregnant woman, but may also be applied to other locations of the body of the pregnant woman.

The physiological measurement system may provide an analogue electrophysiological signal or a digital electrophysiological signal. A digital electrophysiological signal has at least a large enough sampling frequency to transfer with the digital signal relevant information relating to uterus muscle activity. The sampling frequency may be, for example, at least 10 Hz.

Capacitive electrodes are relatively comfortable because they do not need to be fixed onto the skin by using a gel or adhesive. Therefore, applying the capacitive electrode may be done more efficiently.

Optionally, the physiological measurement system comprises more than two cutaneous or capacitive electrodes for measuring signals of uterine muscle activity of a pregnant woman. The physiological measurement system is further configured to provide at least two electrophysiological signals to the input of the signal processing arrangement. In accordance with a previously discussed embodiment, the signal processing arrangement may be configured to use the information of the at least two electrophysiological signals to generate a more reliable output waveform. It is to be noted that, when the physiological measurement system comprise three electrodes, three different electrophysiological signals may be generated, namely, a first signal measured between a first electrode and a second electrode, a second signal measured between the second electrode and a third electrode, and a third signal measured between the first electrode and the third electrode.

According to a third aspect of the invention, a signal processing method of processing electrophysiological signals relating to uterine contractions of a pregnant woman is provided. The signal processing method comprises the stages of a) receiving an electrophysiological signal representing uterine muscle activity of a pregnant woman, b) filtering the received electrophysiological signal to obtain a filtered electrohysterogram signal, the filtering is according to a filter which allows the passage of frequencies of the electrophysiological signal in a first frequency range and for attenuating frequencies of the electrophysiological signal outside the first frequency range, the first frequency range is from 0 Hz to 3 Hz, c) generating an output waveform by continuously applying a window function to samples of the filtered electrohysterogram signal, wherein a single application of the window function comprises adding, according to the window function, samples of the filtered electrohysterogram signal of an interval of time preceding the application of the window function, and d) providing the output waveform, the output waveform simulates output data of a tocodynamometer or an intra-uterine pressure catheter representing data relating to uterine contractions.

The signal processing method according to the third aspect of the invention provides the same benefits as the signal processing arrangement according to the first aspect of the invention and has similar embodiments with similar effects as the corresponding embodiments of the arrangement.

According to a fourth aspect of the invention, a monitoring method of monitoring uterine contractions of a pregnant woman is provided. The monitoring method comprises the stage of a) receiving signals being obtained by non-invasive electrophysiological measurements from the abdomen of the pregnant woman by means of at least two cutaneous or capacitive electrodes being placed on the abdomen of the pregnant woman, b) amplifying and digitalizing the received signals to obtain an electrophysiological signal, and comprises the stages of the signal processing method of the third aspect of the invention.

The monitoring method according to the fourth aspect of the invention provides the same benefits as the signal processing arrangement according to the first aspect of the invention and the monitoring system according to the second aspect of the invention and has similar embodiments with similar effects as the corresponding embodiments of the arrangement and/or system.

According to a fifth aspect of the invention, a computer program product is provided which comprises instructions for causing a processor system to perform the stages of signal processing method of the third aspect of the invention or to perform the stages of the monitoring method of the fourth aspect of the invention.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

Modifications and variations of the arrangement, the system, the method, and/or of the computer program product, which correspond to the described modifications and variations of the arrangement or the system, can be carried out by a person skilled in the art on the basis of the present description.

Figure 1:
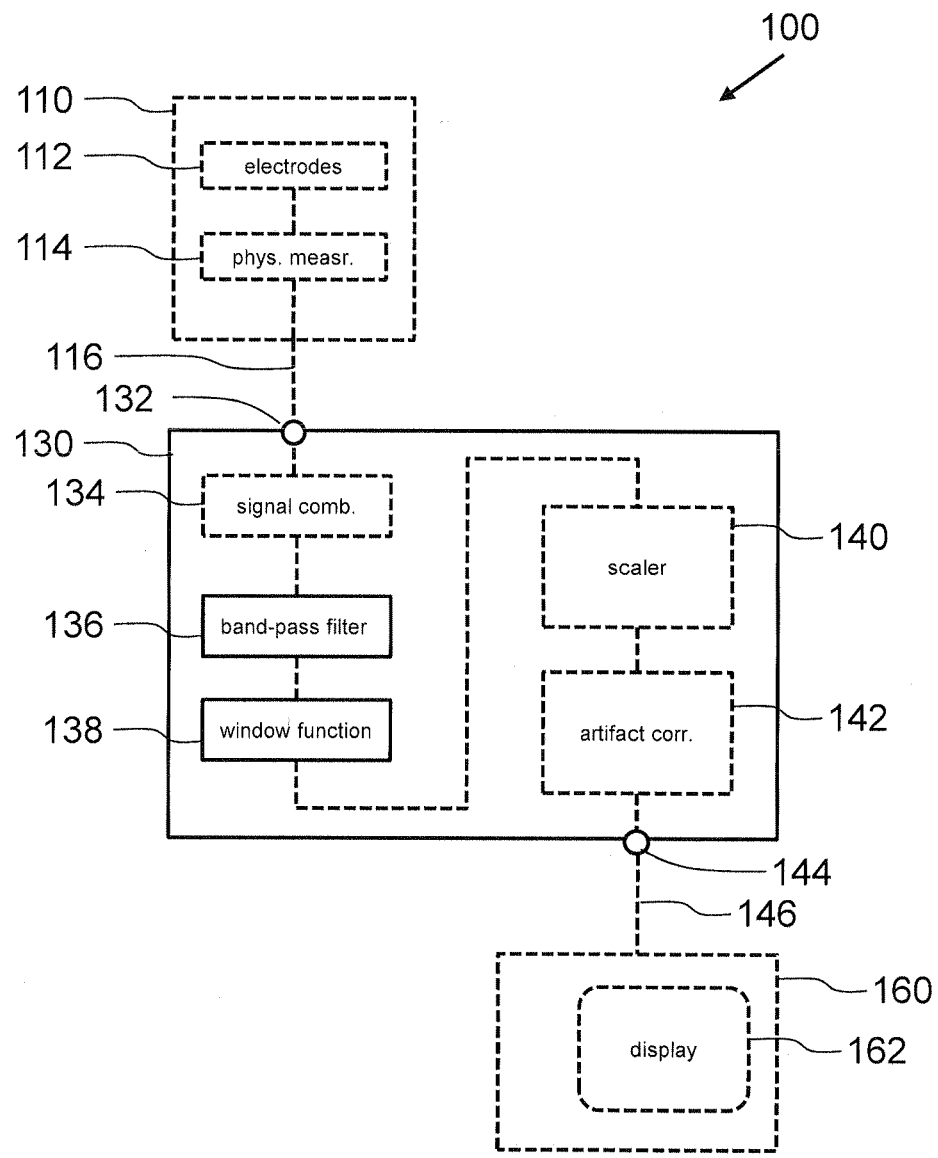
FIG. 1 schematically shows a monitoring system comprising a signal processing arrangement, respectively, according to the second aspect and the first aspect of the invention, FIGS. 2a and 2b schematically show other embodiments of a monitoring system according to the second aspect of the invention.

It should be noted that items denoted by the same reference numerals in different Figures have the same structural features and the same functions, or are the same signals. Where the function and/or structure of such an item have been explained, there is no necessity for repeated explanation thereof in the detailed description.

The Figures are purely diagrammatic and not drawn to scale. Particularly for clarity, some dimensions are exaggerated strongly.

DETAILED DESCRIPTION

A first embodiment is shown in FIG. 1. FIG. 1 schematically shows a monitoring system 100 which comprises a physiological measurement system 110, a signal processing arrangement 130, and an optional presentation device 160.

The physiological measurement system 110 comprises at least two cutaneous or capacitive electrodes 112 which form a sensor for measuring activity of the muscles of the uterus of a pregnant woman. The at least two cutaneous or capacitive electrodes 112 are coupled to a physiological measurement circuit 114 which uses the two cutaneous or capacitive electrodes 112 to provide an electrophysiological signal 116. The physiological measurement circuit 114 at least amplifies the signal provided by the two cutaneous or capacitive electrodes 112 and may optionally digitalize the amplified signal. Different physiological measurement systems are known in the art and may be used in the monitoring system 100. The used physiological measurement system 110 must be suitable for measuring electrical activity related to the muscles of the uterus of a pregnant woman. In use, this means that the at least two cutaneous or capacitive electrodes 112 must be applied to the abdomen of the pregnant woman.

The signal processing arrangement 130 at least comprises an input 132, a band-pass filter 136, a window function applicator 138 and an output 144. Optionally, the signal processing arrangement 130 comprises a signal combination means 134, a signal scaling means 140 and an artifact correction means 142.

The input 132 receives at least one electrophysiological signal 116 which comprises information that relates to uterine muscle activity of a pregnant woman. As discussed above, a known physiological measurement system 110 may provide this signal. The electrophysiological signal 116 may comprise information which relates to all kind of electrical activities in the cells and tissues of the abdomen of a pregnant woman and may comprise noise.

The electrophysiological signal 116 is provided to a band-pass filter 136 which allows a passage of frequencies of the electrophysiological signal in a first frequency range and which is configured to attenuate frequencies of the electrophysiological signal outside the first frequency range. In a specific embodiment, the first frequency range is from 0.1 Hz to 3 Hz. In another specific embodiment, the first frequency range is from 0.2 Hz to 2 Hz. In a further specific embodiment, the first frequency range is from 0.3 Hz to 0.8 Hz. The measured uterine muscle activity is, for the largest parts, present in the provided first frequency ranges. The band-pass filter provides a filtered electrohysterogram signal. An example of the band-pass filter will be discussed later. In the context of the invention, it is to be noted that, a low-pass filter may be used instead of the band-pass filter 136. Such a low-pass filter does not attenuate frequencies below an upper limit frequency and attenuates frequencies above the upper limit frequency. In an embodiment, the upper limit frequency is 3 Hz, and in another embodiment, the upper limit frequency is 0.8 Hz.

The window function applicator 138 receives from the band-pass filter 136 the filtered electrohysterogram signal and applies a specific window function such that the window function applicator 138 provides an output signal 146 which simulates output data of a tocodynamometer or an intra-uterine pressure catheter representing data relating to uterine contractions. Before the window function is applied, the window function applicator 138 rectifies the received filtered electrohysterogram signal such that samples of the filtered electrohysterogram signal represent absolute values of the electrohysterogram signal. The window function has a specific shape and smoothens the filtered electrohysterogram signal which results in a signal in which a rising edge and a descending edge of an obtained pulse in the output waveform is almost similar to the shape of the pulses measured with a tocodynamometer or an intra-uterine pressure catheter. The timing of the pulse of the output waveform must also match the timing of the pulses measured with the tocodynamometer or an intra-uterine pressure catheter. The window function applicator 138 continuously applies the window function to samples of the filtered electrohysterogram signal to continuously calculate samples of the output waveform. When, at a specific moment in time a sample of the output waveform is calculated, the window function applicator 138 only adds, according to weight values provided by the applied window function, absolute values of samples of the filtered electrohysterogram signal which relate to a specific time interval that immediately precedes the moment in time at which the window function is applied. In general a skilled person knows how a window function needs to be applied to a specific digital input signal and how this application results in a specific digital output signal and the window function applicator applies the window function in such a manner. However, often, the window function defines that if the nth sample of the output signal must be calculated, samples of the input signal in a sequence which starts before the nth sample of the input signal and which ends after the nth sample of the input signal must be used in the calculation. In the specific situation of the invention, no samples after the nth sample of the input signal are being used. This results in the prevention of long signal processing delays in the window function applicator 138. In an embodiment, the length of the specific interval of time is at least 15 seconds, and may be, in an optional embodiment, in between 19 and 26 seconds. In another specific embodiment, the length of the specific interval of time is in between 20 and 25 seconds. In yet a further specific embodiment, the length of the specific interval is 21 seconds. Examples of specific window functions will be discussed later.

Optionally, the input 132 of the signal processing arrangement 130 receives a plurality of electrophysiological signals relating to muscle activity of a single pregnant woman. The plurality of electrophysiological signals may be provided by the physiological measurement system 110 when the physiological measurement system 110 comprises more than two cutaneous or capacitive electrodes. At least each combination of two electrodes is capable of providing an electrophysiological signal 116. If the input 132 of the signal processing arrangement receives a plurality of electrophysiological signals, the signal processing arrangement 130 may comprise a signal combination means 134 which combines the received plurality of electrophysiological signals into a single electrophysiological signal and provides the single electrophysiological signal to the band-pass filter 136. The signal combination means 134 may be configured to form the single electrophysiological signal by combining the plurality of electrophysiological signals. The combining of the signals may comprise the creation of a linear combination of the signals, but may also comprise that specific signals are multiplied with each other. In this way more information is measured and, as such, a more reliable simulation of the output data of a tocodynamometer or an intra-uterine pressure catheter can be obtained.

Depending on the specific use of the output waveform 146, the output waveform 146 has to be within a predefined dynamic range, for example, in between 0 and 5 millivolts, or, when the signal is provided in a digital manner, for example, between 0 and 255. In order to obtain such a signal, the output signal of the window function applicator 138 may be provided to the signal scaling means 140 which scales the signal into the required dynamic range. In a further embodiment of the signal scaling means 140, the scaling means may be configured to apply a scaling factor which is based on a maximum of the output signal of the window function applicator 138 during a predefined time interval, for example, a time interval of 5 minutes. Subsequently, this determined maximum value of the predefined time interval may be mapped onto 70% of the maximum possible value of the dynamic range, such that, when the uterine muscle activity increases in strength, the output waveform may increase but is still within the dynamic range. The predefined time interval may, for example, be the first 5 minutes starting from the moment in time when the signal processing arrangement 130 was coupled to an electrophysiological signal 116. The predefined time interval may also be a time interval of 5 minutes which immediately precedes a moment in time when a user of the signal processing arrangement provides a calibration command (e.g. via a calibration button).

In a further optional embodiment of the signal processing arrangement 130, the artifact correction means 142 is provided which filters out artifacts from the output waveform. Artifacts are signal components which do not relate to a signal which has to represent output data of a tocodynamometer or an intra-uterine pressure catheter. An artifact may also be a signal component that is the result of information in the electrophysiological signal which does not relate to uterine muscle activity. The artifact correction means 142 may be configured to detect specific waveform shapes which clearly do not relate to uterine muscles activity. The artifact correction means 142 may also be configured to analyze the received electrophysiological signal 116 or to analyze a plurality of received electrophysiological signals to find the presence of signal components which seems not to relate to uterine muscles activity, such as noise, and to use the found information to delete artifacts from the output waveform. The artifact correction means 142 may also be coupled to additional sensors which provide, for example, information about movements of the pregnant woman—such movements may lead to distortions of the electrophysiological signals that may affect the output waveform while not relating to uterine contractions.

The output waveform 146 is provided at the output 144 of the signal processing arrangement 130. The output waveform 146 may be provided to an optional presentation device 160 which is suitable for presenting signals which originate from a tocodynamometer or an intra-uterine pressure catheter. Such a presentation device 160 comprises, for example, a display 162 on which the output waveform is being presented. The presentation device 160 may also comprise a plotter which draws the output waveform on paper. In yet another embodiment of the presentation device 160, the presentation device presents in a numerical display the actual value of the output waveform and/or the average time between uterine contractions, or the average number of uterine contractions per hour. In relatively simple embodiment of the presentation device 160, the presentation device 160 comprises a light source that emits light if the output waveform 146 indicates that an uterine contraction has been detected.

FIG. 1 is a schematic drawing which presents a specific grouping of functional units in the physiological measurement system 110, the signal processing arrangement 130, and the presentation device 160. However, the invention is not limited to this specific grouping of functional units. All functional units may be integrated in a single device, or functional units of the signal processing unit may be spread over several devices. It is also possible that some functional units are integrated in a single piece of dedicated hardware, or that the functionality of some functional units is provided by a signal processor that operates under the control of a specific computer program product.

Figure 2A:
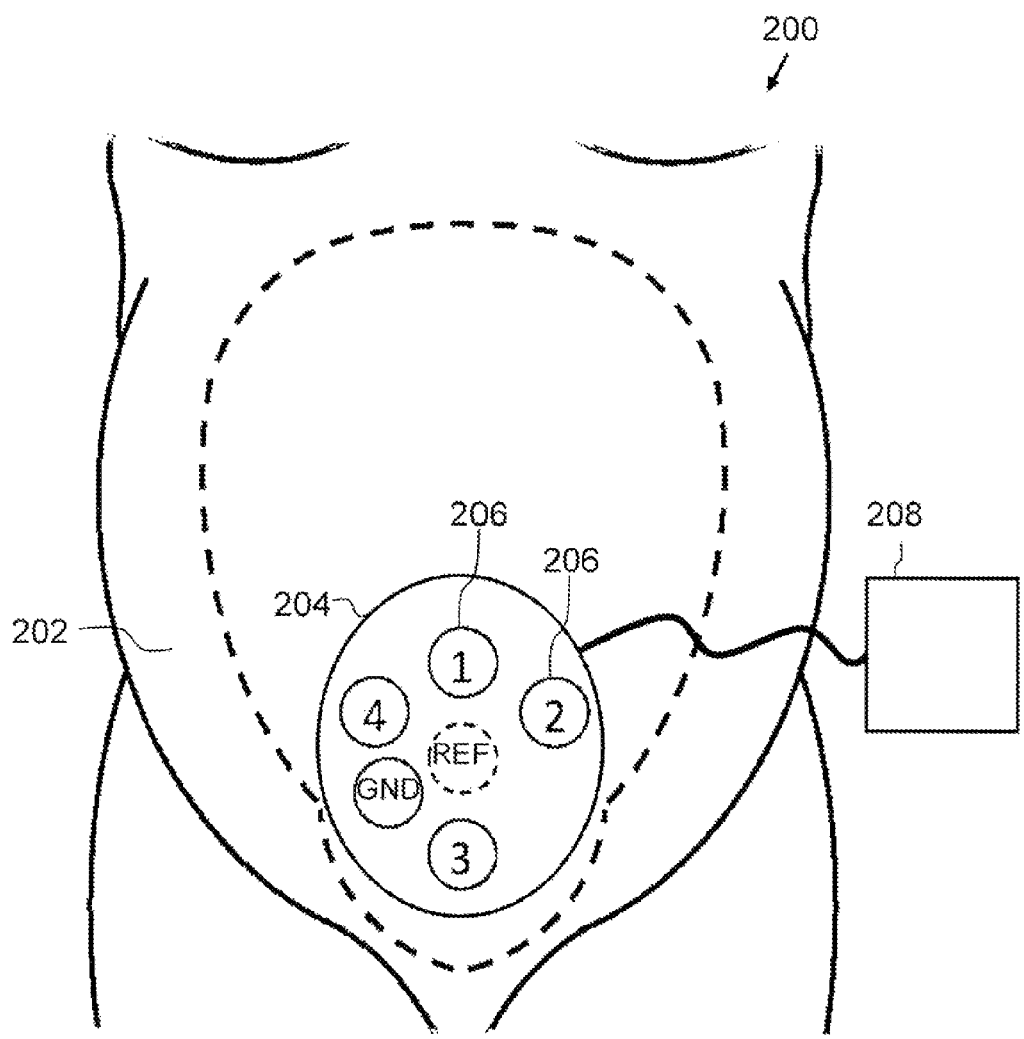
Figure 2B:
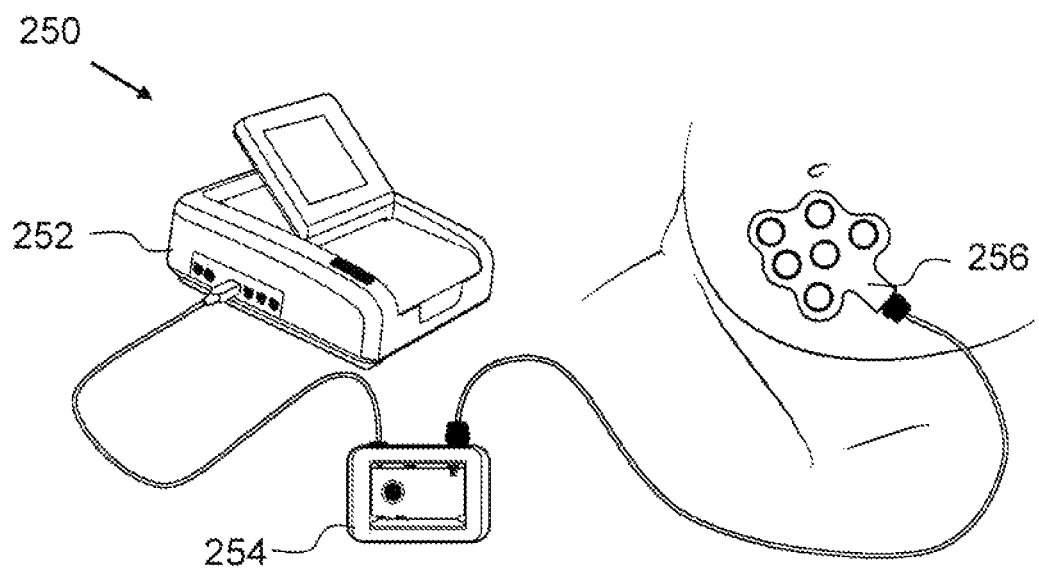

FIGS. 2*a* and 2*b* schematically show other embodiments of a monitoring system 200, 250 according to the second aspect of the invention.

In FIG. 2*a* a body 202 of a pregnant woman is schematically drawn. In use, the monitoring system 200 comprises a plurality of cutaneous or capacitive electrodes 1, 2, 3, 4, GND, REF, 206 which are brought in contact with the abdomen of the pregnant woman. In the specific embodiment of FIG. 2*a*, the electrodes 1, 2, 3, 4, GND, REF, 206 are integrated in a single patch or plaster 204 such that, with a single action, all electrodes may be positioned on the abdomen of the woman. The plaster 204 is connected to a device 208 which comprises additional circuitry of the previously discussed physiological measurement system and the previously discussed signal processing arrangement.

FIG. 2*b* presents another exemplary embodiment of a monitoring system 250 according to the second aspect of the invention. A patch 256 with a plurality of electrodes is, in use, applied to the abdomen of a pregnant woman. The path 256 is coupled with a wire to a signal processing device 254 which is capable of generating and/or measuring a plurality of electrophysiological signals on basis of the electrical signals received at the electrodes of the path 256, and which is capable of processing the plurality of electrophysiological signals with a signal processing arrangement according to the first aspect of the invention (see, for example, the embodiments of the signal processing arrangement 130 of FIG. 1). The signal processing device 254 provides an output waveform which simulates output data of a tocodynamometer or an intra-uterine pressure catheter. There are predefined formats for the output data of a tocodynamometer or an intra-uterine pressure catheter and the provided output waveform fulfills these standards. As such the output waveform may be provided to a tocodynamometer/intra-uterine pressure catheter output data presentation device 252 which makes the output waveform of the signal processing device 254 visible or audible to a user of the monitoring system 250. The tocodynamometer/intra-uterine pressure catheter output data presentation device 252 may also comprise a data storage for (at least temporarily) storing data of the output waveform and may also comprise a network interface for transmitting the data of the output waveform via a network to another device.

It is to be noted that several devices and/or elements of FIG. 2*a* and FIG. 2*b* are connected to each other via wires. In alternative embodiments, the devices and/or elements comprise additional wireless communication circuitry to transmit and receive relevant signals and waveforms of the monitoring systems 200, 250 via a wireless transmission channel.

Figure 3:
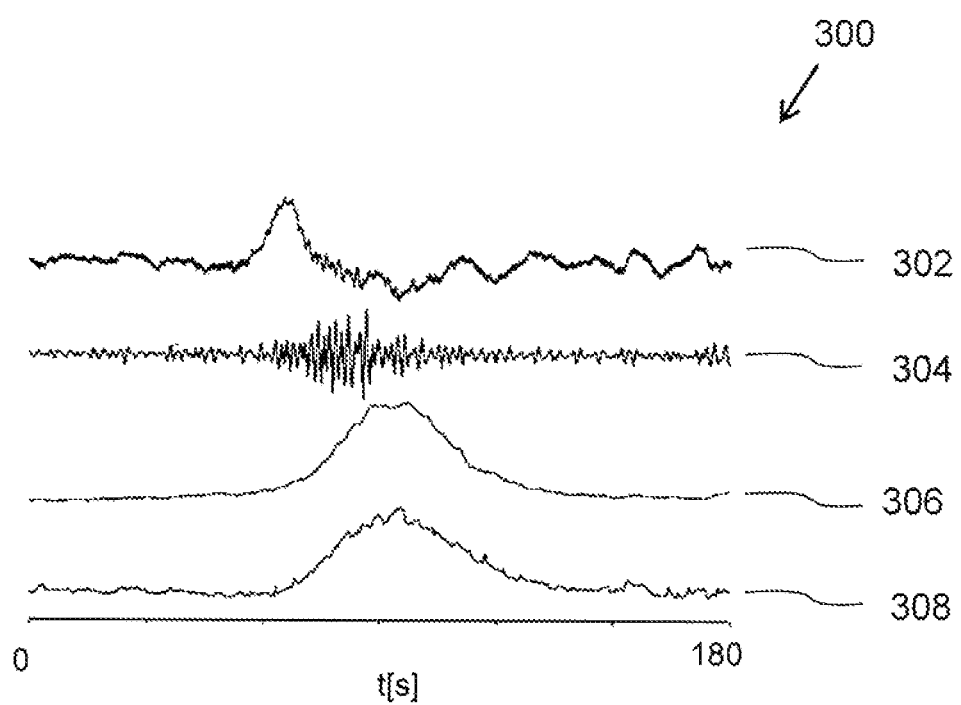
FIG. 3 shows examples of different signals being processed by the signal processing arrangement and shows a signal that has been measured with an intra-uterine pressure catheter.

FIG. 3 shows examples of different signals 302, 304, 306 being processed by the signal processing arrangement and shows a signal 308 that has been measured with an intra-uterine pressure catheter. Signal 302 is the received electrophysiological signal. After applying the band-pass filter to signal 302, signal 304 is obtained. Signal 304 represents an example of a filtered electrohysterogram signal. The applied band-pass filter allows the passage of spectral components in between 0.3 Hz and 0.8 Hz and has characteristics in accordance with an embodiment of a band-pass filter which is discussed in the context of FIG. 4a. Subsequently, a specific window function is applied to signal 304 to obtain signal 306. Signal 306 is the generated output waveform which is based on the input electrophysiological signal 302. The applied specific window function has characteristics in accordance with an embodiment of a window function which is discussed in the context of FIG. 4b. Signal 308 is a signal which is measured at the same moment in time with an intra-uterine pressure catheter. As can be seen in FIG. 3, the output waveform of signal 306 has almost the same shape and (relative) intensity level as the signal of the intra-uterine pressure catheter. Thus, the signal processing arrangement of the first aspect of the invention is well capable of simulating output data of a tocodynamometer or an intra-uterine pressure catheter.

Figure 4A:
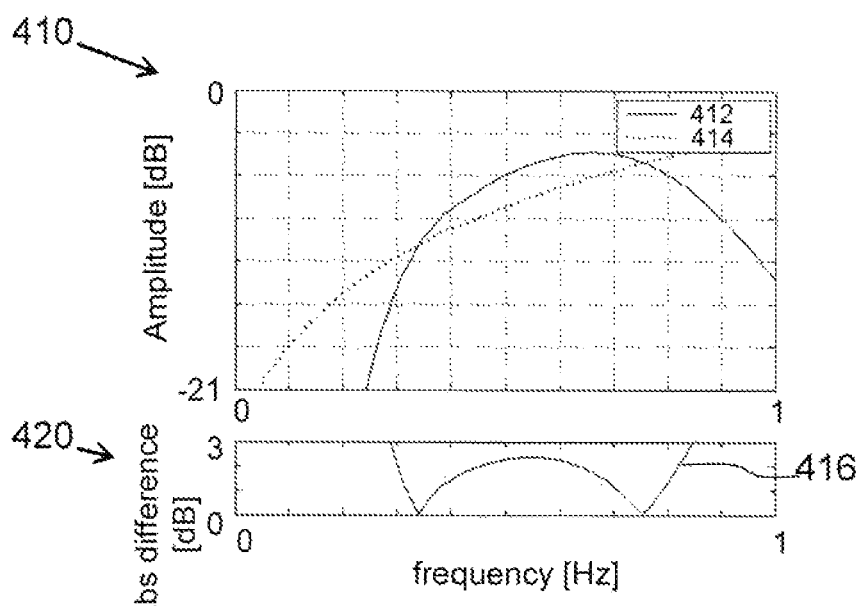
FIG. 4a shows characteristics of an example of a band-pass filter.

FIG. 4a shows characteristics of an example of a band-pass filter. In the context of this invention, the amplitude response of the band-pass filter linearly increases with the frequency within the first frequency range. In practical embodiments it is very difficult to create a filter which exactly linearly increases with the frequency. Thus, in a practical embodiment, the real amplitude response of the band-pass filter may deviate with a maximum error value from this linear increasing amplitude response. In chart 410 the x-axis represents the frequency and the y-axis represents the amplitude response of the band-pass filter (drawn in a dB scale). Line 414 is the ideal linear response line. Line 412 is an example of an amplitude response of a practical embodiment of the band-pass filter which allows the passage of spectral components in between 0.3 Hz and 0.8 Hz and has to attenuate spectral components outside this range. Chart 420 shows the difference between the ideal linear response 414 and the amplitude response 412 of the practical embodiment of the band-pass filter. The x-axis of chart 420 represents the frequency and the y-axis represents the absolute difference (on a dB scale). As may be seen in chart 420, the absolute difference is smaller than 3 dB and, as such, the amplitude response 412 of the practical embodiment of the band-pass filter is almost linear in the spectral range from 0.3 Hz to 0.8 Hz.

The phase response of the band-pass filter is not shown. In practical embodiments, the band-pass filter is implemented as a Finite Impulse Response filter which implies that the phase response, in the relevant spectral range from 0.3 Hz to 0.8 Hz, is linear with respect to the frequency.

Figure 4B:
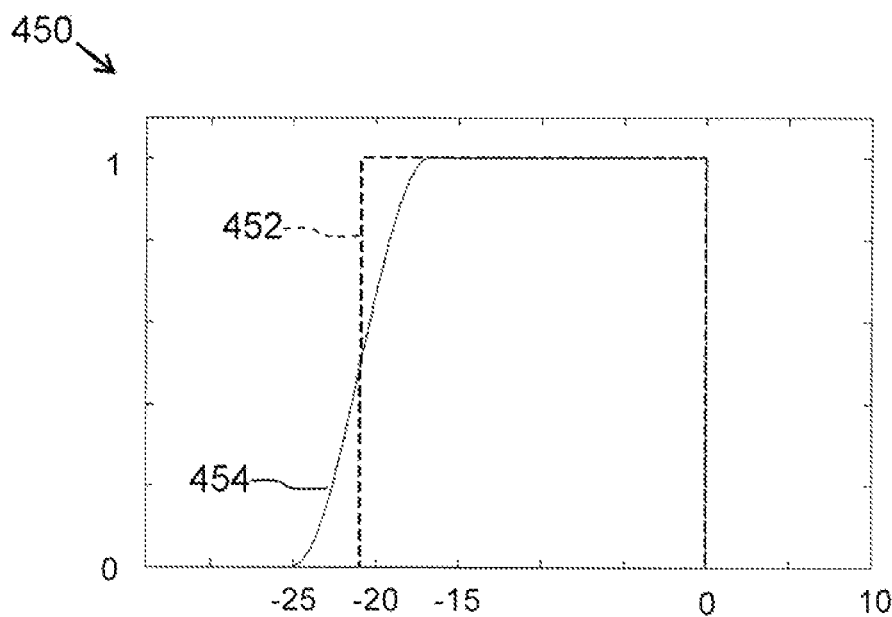
FIG. 4b shows characteristics of two examples of a window function, and FIG. 5 schematically shows an example of a signal processing method and a monitoring method.

FIG. 4b shows characteristics of two examples 452, 454 of a window function. In chart 450 the two examples are provided. The x-axis represents the time-axis and the reference point 0 relates to the moment in time for which a new sample of the output waveform is being calculated. The y-axis represents the value of the window function. The value defines with which value a specific sample of the filtered electrohysterogram signal must be added to the calculated new sample of the output waveform. It should be noted that, often, after applying the window function, the calculated new value of the output waveform is normalized. Window function 452 defines that all samples of the filtered electrohysterogram signal in the interval of time between 21 seconds before the reference point 0 and the reference point 0 must be added with equal weight factors. Window function 454 defines this also for the samples in between 15 and 0 second before the reference point 0, and defines that samples in between 25 and 15 seconds before the reference point 0 should be added to the calculated new value of the output waveform with increasing weight factors (increasing from low at 25 second to high at 15 seconds before the reference point 0. Window function 454 results in a smoother output waveform.

Figure 5:
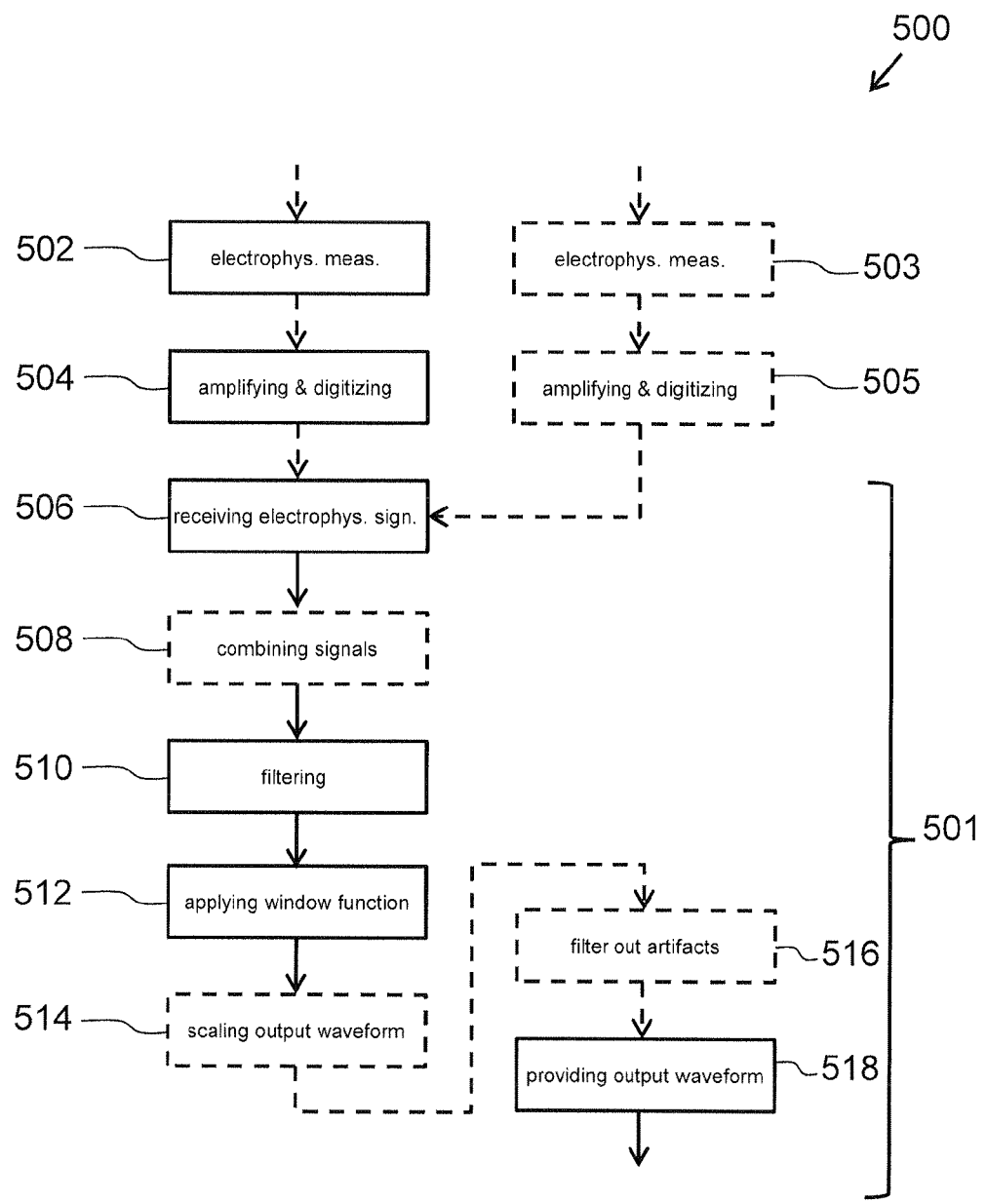

FIG. 5 schematically shows an example of a signal processing method 501 and a monitoring method 500. As shown in FIG. 5, the monitoring method 500 comprises the signal processing method 501. The signal processing method 501 is used to process electrophysiological signals which are related to uterine contractions of a pregnant woman. The monitoring method 500 is used for monitoring uterine contractions of the uterus of a pregnant woman. Boxes that are drawn with a dashed line are optional stages in the methods.

In stages 502 and 503 signals may be obtained by non-invasive electrophysiological measurements from the abdomen of the pregnant woman. The signals are obtained with cutaneous or capacitive electrodes which are placed on the abdomen of the pregnant woman. In stages 504 and 505 the signal received by the cutaneous or capacitive electrodes are amplified and digitized to obtain in each one of the stage-branches 502/504, 503/505 an electrophysiological signal. As shown in FIG. 5, in the monitoring method, at least one electrophysiological signal is obtained and in an optional embodiment a plurality of electrophysiological signals is obtained.

In stage 506 of the signal processing method 501, at least one electrophysiological signal is received which comprises information that relates to uterine muscle activity of a pregnant woman.

In optional stage 508, if a plurality of electrophysiological signals is received, the plurality of electrophysiological signals is combined into a single electrophysiological signal. In an embodiment, the combining may be done by forming a linear combination of the plurality of electrophysiological signals.

In stage 510, the (single) electrophysiological signal is filtered to obtain a filtered electrohysterogram signal. The filtering is based on a band-pass filter which allows the passage of frequencies of the electrophysiological signal in a first frequency range and for attenuating frequencies of the electrophysiological signal outside the first frequency range. The first frequency range is from 0 Hz to 3 Hz.

In stage 512, an output waveform is generated by continuously applying a window function to samples of the filtered electrohysterogram signal. A single application of the window function comprises adding, according to the window function, samples of the filtered electrohysterogram of an interval of time preceding the application of the window function.

Optionally, before the output waveform is generated by applying the window function, the filtered electrohysterogram signal is rectified such that the window function is applied to absolute values of the filtered electrohysterogram signal.

Optionally, in stage 514, the output waveform is scaled such that it falls within a predefined dynamic range.

Optionally, in stage 516, artifacts not relating to uterine contractions are filtered out of the output waveform.

In stage 518, the output waveform is provided. The output waveform simulates output data of a tocodynamometer or an intra-uterine pressure catheter representing data relating to uterine contractions.

According to another aspect of the invention, a computer program product is provided. The computer program product comprises instructions for causing a processor system to perform the stage of any one of the above discussed methods. The computer program product may comprise instructions for a processor of a general purpose computer or, in another embodiment, the computer program product comprises instructions for a signal processor.

In a summary, the current invention provides a signal processing arrangement, a monitoring system, a signal processing method, a monitoring method of monitoring uterine contractions of a pregnant woman, and a computer program product. The signal processing arrangement receives an electrophysiological signal representing uterine muscle activity of a pregnant woman at an input. A filter generates a filtered electrohysterogram signal from the electrophysiological signal. The filter allows the passage of spectral components between 0 and 3 Hz. A window function applicator applies a window function to the filtered electrohysterogram signal to obtain an output waveform. The window function defines that samples of a time interval preceding the application of the window function need to be used The output waveform simulates output data of tocodynamometer or an intra-uterine pressure catheter. The output waveform is provided at an output of the signal processing arrangement.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the arrangement or system claim enumerating several means, several of these means may be embodied by one and the same item of hardware. The mere fact that certain measures are recited in mutually different dependent claims does not indicate that a combination of these measures cannot be used to advantage.

The invention claimed is:

1. A signal processing arrangement for processing electrophysiological signals related to uterine contractions of a pregnant woman, the signal processing arrangement comprising:
   an input for receiving an electrophysiological signal that is measured on the abdomen of a pregnant woman,
   a band-pass filter for receiving the electrophysiological signal and for providing a filtered electrohysterogram signal, the filter being configured to allow a passage of frequencies of the electrophysiological signal in a frequency band and to attenuate frequencies of the electrophysiological signal outside the frequency band, the frequency band lying in a range from 0 Hz to 3 Hz,
   a window function applicator for receiving the filtered electrohysterogram signal from the band-pass filter and for providing an output waveform, the window function applicator being configured to generate the output waveform by continuously applying a window function to samples of the filtered electrohysterogram signal, wherein a single application of the window function comprises adding, according to weight values provided by the applied window function, only absolute values of samples of the filtered electrohysterogram signal which relate to a specific time interval that immediately precedes the moment in time at which the window function is applied, and
   an output for providing the output waveform, the output waveform simulating output data of a tocodynamometer or an intra-uterine pressure catheter, the output data representing data relating to uterine contractions.

2. The signal processing arrangement according to claim 1, wherein the filter has in the frequency band an amplitude response which linearly increases, within the limits of a predefined error value, with the frequency.

3. The signal processing arrangement according to claim 2, wherein the predefined error value is 6 dB.

4. The signal processing arrangement according to claim 1, wherein a length of the time interval is larger than 15 seconds.

5. The signal processing arrangement according to claim 1, wherein the window function has a value of one for samples of the filtered electrohysterogram signal which fall within a sub-interval of time from 0 to 15 seconds preceding the application of the window function.

6. The signal processing arrangement according to claim 1, wherein the frequency band is from 0.1 to 3 Hz.

7. The signal processing arrangement according to claim 6, wherein the frequency band is from 0.3 to 0.8 Hz.

8. The signal processing arrangement according to claim 1, wherein the input is configured to receive a plurality of electrophysiological signals representing uterine muscle activity of a pregnant woman, and wherein the plurality of electrophysiological signals are combined into a single electrophysiological signal and the filter receives the single electrophysiological signal.

9. The signal processing arrangement according to claim 1, wherein the signal processing arrangement further comprises a signal scaler for scaling the output waveform to a waveform within a predefined dynamic range before the output waveform is provided to the output.

10. The signal processing arrangement according to claim 1, wherein the signal processing arrangement further comprises an artifact corrector for filtering out information from the output waveform which does not relate to uterine contractions before the output waveform is provided to the output.

11. A monitoring system for monitoring uterine contractions of a pregnant woman, the monitoring system comprising:
    a physiological measurement system for providing the electrophysiological signal, the physiological measurement system comprising at least two cutaneous or capacitive electrodes for measuring signals of uterine muscle activity of a pregnant woman,
    a signal processing arrangement according to claim 1, the input of the signal processing arrangement being coupled to the physiological measurement system.

12. The monitoring system according to claim 11, wherein the physiological measurement system comprises more than two cutaneous or capacitive electrodes for measuring signals of uterine muscle activity of a pregnant woman and the physiological measurement system is configured to provide at least two electrophysiological signals to the input of the signal processing arrangement.

13. The signal processing arrangement according to claim 1, wherein the output provides the output waveform to a presentation device for interpretation.

14. The signal processing arrangement according to claim 1, wherein the output provides the output waveform to a presentation device for interpretation by a doctor.

15. A signal processing method of processing electrophysiological signals related to uterine contractions of a pregnant woman, the signal processing method comprising the stages of:
   obtaining via a plurality of electrodes and a measurement device an electrophysiological signal representing uterine muscle activity of a pregnant woman,
   receiving at an input the electrophysiological signal,
   filtering the received electrophysiological signal to obtain a filtered electrohysterogram signal, the filtering being performed using a filter which allows the passage of frequencies of the electrophysiological signal in a frequency band and for attenuating frequencies of the electrophysiological signal outside the frequency band, the frequency band lying in a range from 0 Hz to 3 Hz,
   receiving at a window function applicator the filtered electrohysterogram signal and generating an output waveform by the window function applicator continuously applying a window function to samples of the filtered electrohysterogram signal, wherein a single application of the window function by the window function applicator comprises adding, according to weight values provided by the applied window function, only absolute values of samples of the filtered electrohysterogram signal which relate to a specific time interval that immediately precedes the moment in time at which the window function is applied,
   providing via a presentation device the output waveform for interpretation, the output waveform simulating output data of a tocodynamometer or an intra-uterine pressure catheter representing data relating to uterine contractions.

16. A monitoring method of monitoring uterine contractions of a pregnant woman, the monitoring method comprising the stages of:
   receiving signals obtained by non-invasive electrophysiological measurements from the abdomen of the pregnant woman by means of at least two cutaneous or capacitive electrodes being placed on the abdomen of the pregnant woman,
   amplifying and digitalizing the signals received in the receiving signals stage to obtain an electrophysiological signal, and
   further comprising the stages of the signal processing method of claim 15.

17. A non-transitory tangible computer program product comprising instructions for causing a processor system to perform the stages of the method of claim 15.

18. The signal processing method according to claim 15, wherein the output waveform is provided to the presentation device for interpretation by a doctor.

* * * * *